US009824446B2

(12) United States Patent
Littell

(10) Patent No.: US 9,824,446 B2
(45) Date of Patent: Nov. 21, 2017

(54) EVALUATING ELECTROMAGNETIC IMAGERY BY COMPARING TO OTHER INDIVIDUALS' IMAGERY

(71) Applicant: Stephanie Littell, Lexington, MA (US)

(72) Inventor: Stephanie Littell, Lexington, MA (US)

(*) Notice: Subject to any disclaimer, the term of this patent is extended or adjusted under 35 U.S.C. 154(b) by 0 days.

(21) Appl. No.: 14/774,455

(22) PCT Filed: Mar. 14, 2014

(86) PCT No.: PCT/US2014/027765
§ 371 (c)(1),
(2) Date: Sep. 10, 2015

(87) PCT Pub. No.: WO2014/143697
PCT Pub. Date: Sep. 18, 2014

(65) Prior Publication Data
US 2016/0042510 A1  Feb. 11, 2016

Related U.S. Application Data

(60) Provisional application No. 61/799,457, filed on Mar. 15, 2013.

(51) Int. Cl.
G06T 7/00         (2017.01)
G06F 19/00        (2011.01)
A61B 5/00         (2006.01)

(52) U.S. Cl.
CPC .......... *G06T 7/0014* (2013.01); *A61B 5/7271* (2013.01); *G06F 19/321* (2013.01);
(Continued)

(58) Field of Classification Search
None
See application file for complete search history.

(56) References Cited

U.S. PATENT DOCUMENTS 5,810,011 A    9/1998 Kunig
5,933,519 A *  8/1999 Lee ............... G06K 9/00127
                                            382/133
(Continued)

FOREIGN PATENT DOCUMENTS

WO    WO 94/10903      5/1994
WO    WO 2014/143697 A8    9/2014

OTHER PUBLICATIONS

International Preliminary Report on Patentability for International Application No. PCT/US2014/027765, "Evaluating Echocardiographic Imagery by Comparing to Other Patient Imagery," dated Sep. 24, 2015.

(Continued)

*Primary Examiner* — Tsung-Yin Tsai
(74) *Attorney, Agent, or Firm* — Hamilton, Brook, Smith & Reynolds, P.C.

(57) ABSTRACT

A computer-based method and system assists users performing medical imaging studies, such as echocardiograms. While the user manipulates the imaging device on an individual, the system automates image processing, relieving the user from the need to simultaneously operate an application and an imaging device. The system assesses an organ system, then through comparison with other imaging data sets, generates an evaluative assessment of the organ system. The system becomes increasingly image-aware and content-aware during an evaluation, and by sequential comparisons against progressive data sets, refines an evaluative assessment.

19 Claims, 5 Drawing Sheets

(52) U.S. Cl.
CPC ........ *G06F 19/345* (2013.01); *G06F 19/3406* (2013.01); *G06T 2207/10132* (2013.01); *G06T 2207/30048* (2013.01)

(56) References Cited

U.S. PATENT DOCUMENTS

| | | | | |
|---|---|---|---|---|
| 7,536,044 | B2* | 5/2009 | Zhou | G06K 9/6206 382/128 |
| 8,396,268 | B2* | 3/2013 | Zabair | G06K 9/00 128/922 |
| 8,708,914 | B2* | 4/2014 | Suri | G06T 7/0012 382/128 |
| 2002/0095085 | A1 | 7/2002 | Saranathan et al. | |
| 2003/0167010 | A1 | 9/2003 | Pinsky | |
| 2005/0207630 | A1* | 9/2005 | Chan | A61B 6/466 382/131 |
| 2007/0014452 | A1* | 1/2007 | Suresh | G06F 19/3437 382/128 |
| 2007/0081699 | A1 | 4/2007 | Avinash et al. | |
| 2008/0205717 | A1* | 8/2008 | Reeves | G06T 7/0012 382/128 |
| 2011/0098562 | A1* | 4/2011 | Salgo | A61B 8/08 600/437 |
| 2012/0078099 | A1* | 3/2012 | Suri | A61B 8/483 600/440 |
| 2013/0223714 | A1* | 8/2013 | Lipton | G06T 7/0012 382/131 |
| 2016/0022155 | A1 | 1/2016 | Littell | |

OTHER PUBLICATIONS

International Preliminary Report on Patentability for International Application No. PCT/US2014/02799, "Evaluating the Cardiac Engine," dated Sep. 24, 2015.

Anonymous, Telemedicine, Wikipedia, the free encyclopedia, retrieved from the Internet: http://en.wikipedia.org/w/index.php?title= Telemedicine&oldid=567290612, retrieved on Jul. 14, 2014.

Doi, K., "Computer-aided diagnosis in medical imaging: Historical review, current status and future potential", *Computerized Medical Imaging & Graphics*, 31(4-5):198-211 (2007).

Krishnan, S., et al, "Computer-Aided Detection in Echocardiography, Technical Approach for Learned Pattern Recognition", retrieved from the internet: http:/www.healthcare.siemens.com/siemens_hwem-hwem_ssxa_websites-context-root/wcm/idc/siemens_hwem-hwem_ssxa_websites-context-root/wcm/idc/groups/public/@global/@imaging/@ultrasound/documents/download/mdaw/mtil/edisp/whitepaper_krishnan-00064731.pdf, retrieved on Jul. 9, 2014.

Noble, J., et al., "Ultrasound Image Segmentation: A Survey", *IEEE Transactions on Medical Imaging*, 25(8):987-1010 (2006).

Notification of Transmittal of The International Search Report and the Written Opinion of the International Searching Authority, or the Declaration, PCT/US2014/027999, "Evaluating the Cardiac Engine", dated Jul. 15, 2014.

Notification of Transmittal of The International Search Report and the Written Opinion of the International Searching Authority, or the Declaration, PCT/US2014/027765, "Evaluating Electromagnetic Imagery by Comparing to Other Individuals' Imagery", dated Aug. 11, 2014.

Pham, D., et al., "Current Methods in Medical Image Segmentation", *Annu. Rev. Biomed. Eng.*, 2:315-337 (2000).

Yang, L., et al., "Prediction Based Collaborative Trackers (PCT): A Robust and Accurate Approach Toward 3D Medical Object Tracking", *IEEE Transactions on Medical Imaging*, 30(11):1921-1932 (2011).

Young, A., et al., "Computational cardiac atlases: from patient to population and back", *Exp. Physiology*, 94(5):578-596 (2008).

* cited by examiner

EVALUATING ELECTROMAGNETIC IMAGERY BY COMPARING TO OTHER INDIVIDUALS' IMAGERY

RELATED APPLICATIONS

This application is the U.S. National Stage of International Application No. PCT/US/2014/027765 filed Mar. 14, 2014, which designates the U.S., published in English, and claims the benefit of U.S. Provisional Application No. 61/799,457, filed on Mar. 15, 2013. The entire teachings of the above applications are incorporated herein by reference.

BACKGROUND OF THE INVENTION

Viewing one's own pumping heart or working brain has traditionally been the purview of trained experts. For many people, however, the high cost and limited accessibility of imaging devices and methods have prohibited people from obtaining such information.

Traditionally, knowledge of cardiac, vascular or brain functioning has been confined to trained healthcare practitioners. In order to perform the relevant patient study accurately, it takes years to acquire contextual working knowledge of, for example, cardiac patterns. Such patterns are manifested from a wide range of particular cardiac dysfunctions.

Although the investigative tools have become more portable and thus more widely available to primary care providers, usage also requires special training about organ system structure, motion, and cross-modality patterning.

There remains a need to develop devices and methods to conduct medical imaging of vital organs and/or organ systems, and utilize data from the medical imaging field in evaluating the organ or organ system.

SUMMARY OF THE INVENTION

Embodiments of the present invention address the foregoing shortcomings in the art. In particular, the present invention provides a computer-based method and system to assist in performing health imaging in an individual. In certain embodiments, the health imaging includes an echocardiogram.

In one embodiment, the invention relates to a computer-based method of imaging an organ system of an individual. The method comprises automating identification of and recognizing an organ system or an anatomic structure from imaging data acquired through an imaging device, assessing the organ system or anatomic structure of the individual to produce an assessment data set, comparing the assessment data set to one or more comparison data sets in a multi-dimensional classification space to generate an evaluative assessment of the organ system or anatomic structure, wherein the evaluative assessment comprises a classification of the imaging data, and optionally refining the evaluative assessment by repeating the steps of assessing the organ system or anatomic structure and comparing the assessment data.

In certain embodiment, refining the evaluative assessment further comprises optimizing a captured imagery, recording a captured imagery, or a combination thereof, wherein the imaging data is fit into one or more multi-dimensional health classification spaces.

In further embodiments of the invention, the step of automating identification of the organ system or anatomic structure occurs while the imaging device is being used on the individual (i.e., during image acquisition). In certain embodiments, the imaging device comprises one or more sensors.

In another embodiment, the organ system that is assessed is an individual's cardiovascular system, brain, or a combination thereof.

In another embodiment, the invention provides for the method to further comprise animating the motion of the organ system or anatomic structure, creating one or more freeze-frames of the organ system or anatomic structure, abstracting the shape, boundaries, color, textures, or a combination thereof of the organ system or anatomic structure.

In certain embodiments, the one or more sensors is a magnetic sensor, gyroscope, accelerometer, electrocardiography sensor, electromyography sensor, camera, RGB sensor, green light sensor, red light sensor, blue light sensor, motion sensor, near infrared camera, infrared camera, thermal camera, GPS or WiFi.

The present invention also provides for the method to further comprise ranking the individual on a spectrum based on one or more metrics, one or more diagnoses, or combinations thereof, wherein the spectrum is an ordered group of other individuals.

In another embodiment, the method further comprises identifying metrics of the individual based upon the evaluative assessment, wherein the metrics are saved and tracked over a period of time.

In another embodiment, the method further comprises triggering an alert, wherein the alert is generated based on the evaluative assessment. The present invention further provides for the alert to be sent to the individual, a member of the individual's family, an individual's health proxy, a healthcare provider, one or more persons designated by the individual, or a combination thereof.

In another embodiment, the present invention relates to computer system and apparatus to aid in a medical imaging study of an individual. The computer system comprises a recognition module configured to recognize an individual's organ system or anatomic structure to be studied, an assessment module coupled to the recognition module configured to determine morphology and physiology of the recognized organ system or anatomic structure, an evaluation module responsive to the assessment module and configured to identify abnormalities or pathologies in the determined morphology and physiology of said organ system or anatomic structure, if present, a showcase module configured to visually emphasize, abstract, focus, animate, or a combination thereof an image region pertinent to evaluative assessment, an optimization module configured to post-process images, a transmission module configured to send the post-processed images and information to target addresses, and a recommendation module configured to recommend to a user a modification of a view, an angle, an image mode, or a combination thereof.

In certain embodiments, the organ system is a cardiovascular system, a brain, or a combination thereof.

In further embodiments, the computer system further comprises a sensor module configured to connect one or more sensors. In certain embodiments, the one or more sensors is a magnetic sensor, gyroscope, accelerometer, electrocardiography sensor, electromyography sensor, camera, RGB sensor, green light sensor, red light sensor, blue light sensor, motion sensor, near infrared camera, infrared camera, thermal camera, GPS or WiFi.

In one embodiment, the computer system further comprises a ranking module configured to rank the individual based one or more metrics or one or more diagnostic classifications.

In one embodiment, the computer system further comprises a tracking module configured to track metrics of the individual over a period of time, predict a next series of metrics, or a combination thereof.

In another embodiment of the invention, the computer system further comprises a trigger module configured to trigger an alert based on an evaluative assessment or output of the evaluation module. In certain embodiments, the alert is sent to the individual, a member of the individual's family, an individual's health proxy, a healthcare provider, one or more persons designated by the individual, or a combination thereof.

In another embodiment, the medical imaging study is an echocardiogram.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
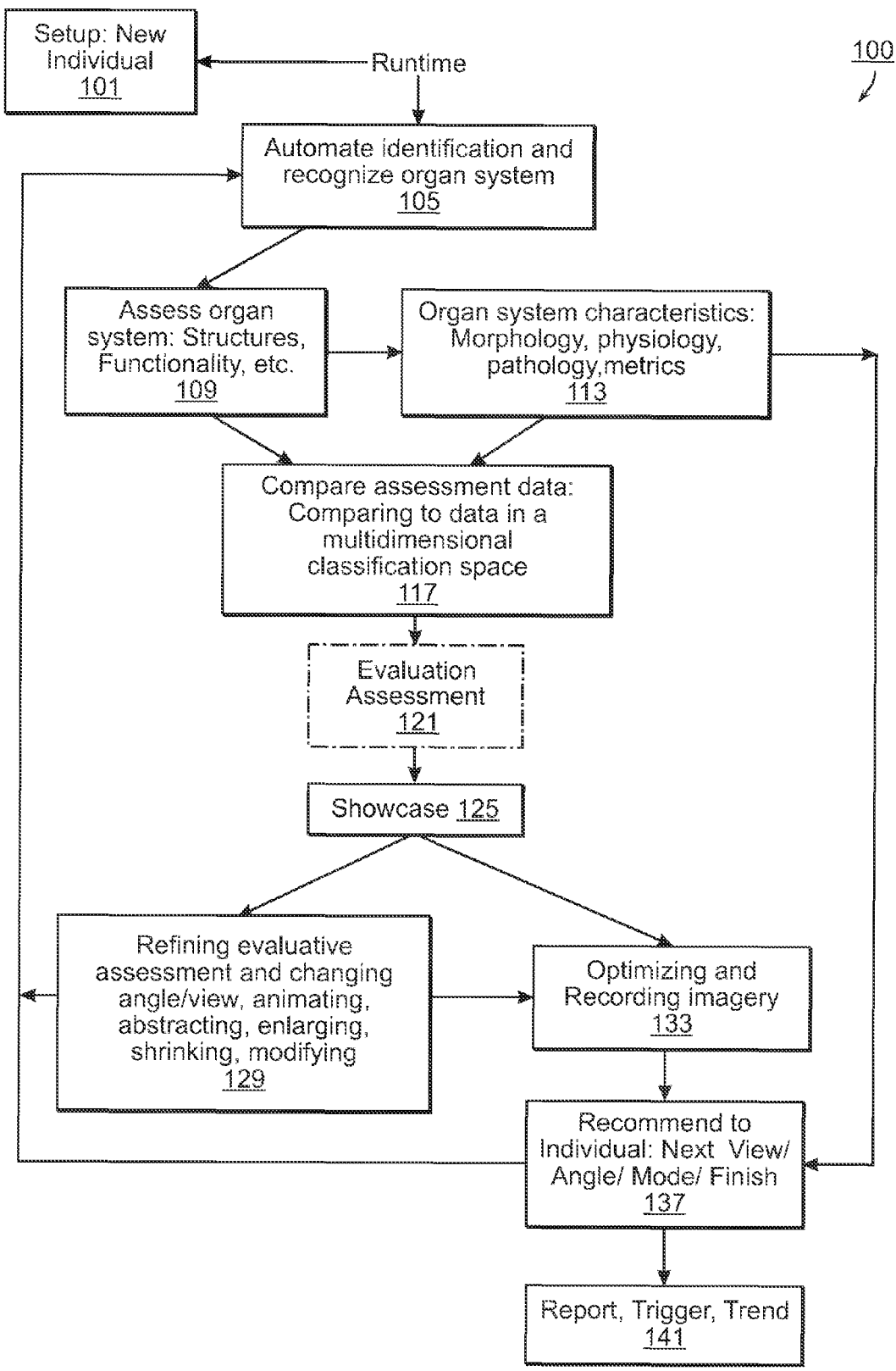
FIG. 1 is a flow diagram of one embodiment of the present invention relating to a computer-based method to perform electromagnetic imaging in an individual.

A description of example embodiments of the invention follows.

Using the methods and tools described herein, medical imaging testing can be achieved practically anywhere worldwide. The digital imaging tools described herein are relatively low-cost and are broadly applicable, allowing more people to receive medical imaging results in adaptable ways. For example, people living in regions with little access to specialized healthcare at, for example, a tertiary care hospital, can undertake specialized diagnostic tests without having to travel to where highly-trained sonographers or physicians work. In other words, medical evaluation can be separated or de-coupled from receiving and interpreting test results. Those trained and specialized in interpreting the evaluation results can be geographically located anywhere.

In emergent situations, sensor, camera and/or device-level information can be electronically communicated or transmitted to a receiving medical facility rather than requiring EMTs, paramedics, or other first responders to fulfill the role of speedy-diagnostic sonographers. Testing can eventually be made possible in low-level medical facilities or even public venues, such that travel and appointment time/cost barriers are lowered.

In order to perform a thorough and well executed patient study in an individual, sonographers and other specialized medical imaging technicians must work years to acquire contextual knowledge of various cardiac patterns, such as patterns manifested from a range of healthy individuals and those with dysfunctions or pathology. To address this training challenge in the medical and healthcare fields, sonographers are generally asked to produce a standard set of echocardiography views. For example, these views could include view-plane slices of the heart showcasing structures, form and functionality.

The invention described herein benefits people who cannot afford to travel to a specialized medical facility, but have access to a technician or physician having little to no experience in echocardiograms. Thus, this computer system helps a technician or sonographer to intelligently choose a set of heart views and images for a patient, that can later be read or reviewed by a more experienced (e.g. licensed) technician or physician.

In order for de-coupling of a medical evaluation from the interpretation of data, diagnostic logic, such as computer-based software, has to orchestrate amongst many disease states so that comparisons are made automatically. Diagnosis of pathology is obtained by using a process of analyzing an individual's morphology, anatomy, and any pathophysiology, and discarding and/or matching the individual's imaging data with kindred identified patterns in hyper-dimensional medical evaluation space. Classifying correctly involves orchestrating such prepared data from the individual against progressive decisions amongst two or more multi-dimensional classifications at each decision-making step. As the ongoing process sufficiently discards certain hypotheses and matches others, showcase regions are derived.

Content-ready imagery ensues as surrounding the showcased regions, and is automatically post-processed for any image optimization. Post-processing involves adjusting noise, gain, brightness and other typical parameters, while ensuring that the diagnostic content of interest is prioritized, rather than using a less consequential diagnostic or evaluation area of imagery. The report that is produced in post-processing imaging content can be tuned for the audience that receives the images. For example, the report that is produced for receipt by a user without medical training can be different than the report that is produced for receipt by a medical professional.

In certain embodiments, this new application aids in the diagnosis of diseases, relying on data provided from the individual and from the individual's geographic locale, rather than upon data from where smaller pools of trained sonographers or physicians and specialists exist.

Further, the application framework described herein can serve other health imaging fields, for example sonography, tomography, radiography, thermography, nuclear medicine, magnetic resonance imaging, and other digital medical imaging fields to decouple testing from results. This application framework can thus serve broader populations, such as those existing in undeveloped regions where only rudimentary healthcare exists.

Automating image processing allows, for example, a user operating a transducer or probe and managing a keyboard subsequently, to minimize upper limb torque and back strain. In order to do so, an embodiment recognizes real-time captured images and content during an imaging study, for example, an echocardiogram. An embodiment also visually recognizes and evaluates an individual's organ system, such as the cardiovascular system, as the user manages the probe appropriately through both major imaging views and fine-tunes angle adjustments upon the individual being studied.

The invention described herein can be used in the medical imaging of a broad variety of organ systems, including, for non-limiting example, the brain, the circulatory system, cardiopulmonary system, cardiovascular system, and the arterial system. A cardiovascular system includes, for example, the heart, the aorta, the aortic arch, and carotid arteries. In certain embodiments, the cardiovascular system also includes facial vasculature, e.g. facial arteries and capillaries, and also the arterial system of the head and neck, including carotid arteries and vertebral arteries.

The present invention includes computer-based methods of imaging an organ system in an individual. The computer-based method described herein is in some instances referred to as an application. In certain embodiments, imaging an organ system is alternately referred to as a health imaging study or a medical imaging study. Imaging data, alternately referred to as medical imaging data, health imaging data, or imaging content, is acquired or generated via an imaging device. In certain embodiments, the imaging device is a transducer or probe. In certain other embodiments, the imaging device comprises at least one of a sensor or a camera. In an example embodiment, the imaging device is an ultrasound device. In certain other embodiments the imaging device further comprises a screen display, a module for emailing or uploading data to a server, the Internet, or a printer and the like. In other embodiments, the imaging device is any electronic device capable of imaging an organ or organ system. For example, an imaging device is a cell phone, tablet, laptop computer, portable device, or handheld computer. In yet further embodiments, imaging data is acquired through an electronic device, such as a cell phone or tablet, with one or more sensors. In example embodiments, the cell phone or tablet further comprises touch controls on its display, such as, for example, a keyboard. In certain other embodiments, the imaging device is an echocardiosystem comprising a probe and a user interface that comprises, for example, a keyboard, knobs, or buttons. In certain embodiments, the imaging device is operated on the individual concurrent with automating identification of an organ system. In another embodiment, the imaging device is operated on the individual concurrent with data processing an assessment data set.

Examples of sensors that can be used in imaging an organ system include magnetic sensors, gyroscopes, accelerometers, electrocardiography sensors, electromyography sensors, cameras, RGB sensors, green light sensors, red light sensors, blue light sensors, motion sensors, near infrared cameras, infrared cameras, thermal cameras, GPS, or WiFi. In an example embodiment, a sensor can be used in conjunction with a position processor such as GPS when the individual is participating in a sporting event, such as a triathlon or a bikeathon. In another example embodiment, a sensor is used with a cell phone's motion processor when an individual is exercising, for example practicing vinyasa yoga.

In certain embodiments, the health imaging study or medical imaging study of the present invention is ultrasound image-based. In certain other embodiments, the study is sonography image-based such as an echocardiography, stress echocardiography, obstetric ultrasonography, abdominal ultrasonography, carotid ultrasonography, intravascular ultrasonography, or pulmonary ultrasound. In specific example embodiments, the medical imaging study is a transthoracic echocardiogram (TTE), transesophageal echocardiogram (TEE), an electrocardiogram (ECG), In alternate embodiments, the health imaging study utilizes the Doppler effect, for example pulsed Doppler or continuous Doppler. An example embodiment of a Doppler-based medical imaging study is transcranial Doppler (TCD).

The user of the methods and computer systems for health imaging disclosed herein can be, for example, a sonographer, a technician, a physician, a patient, or any individual. An individual is alternately referred to herein as a patient.

The computer-based methods of imaging an organ system in an individual further comprise assessing the organ system, resulting in an assessment data set. This assessment data set is compared by the software (executing processor) against comparison data sets, for example selected patient or individual imagery previously collected from the same organ system or anatomical structure in another patient or individual. This comparison yields an evaluative assessment. The "evaluative assessment", as used herein, comprises a classification of the imaging data based on one or more selected properties. For example, an evaluative assessment of an organ system is an assessment based on fluid flow field properties, hemodynamics, cycle timing and gating, chamber-sinus and cross chamber-sinus performance, pulsatility shape, distribution properties such as of oxygen or other nutrients, morphology, geometry, functionality, and other image mode physiology. The evaluative assessment is invoked by the computer system/working processor. In certain embodiments, the step of assessing compiles imaging data.

The assessment data set is compared to one or more comparison data sets, alternately referred to herein as stored data, in a multi-dimensional classification space. Sources of stored data can include medical imaging data stored by a hospital or health care organization/system in, for example, radiology or ultrasound departments, and also include imaging data stored by universities. In alternate embodiments, the source of the stored data can be a data repository containing the medical imaging data of consenting individuals or a Cloud computing device. The stored data that is used for comparison against the assessment data set is prepared data, which is processed in a training set containing both healthy and pathologic imagery. Prior to use in comparisons, such data is processed mathematically via array manipulation, means and variance calculations, weighting, thresholding, iterating, or a combination thereof. Acquired imagery of the individual can undergo analogous mathematical processing, and then be projected into the multi-dimensional classification space. Other image data normalization techniques and the like are suitable.

In certain embodiments, the method described herein further comprises refining the evaluative assessment. The step of refining occurs through collecting another assessment data set from the individual, for example, a data set collected from an alternate imaging view, then comparing this new assessment data set to one or more new comparison data sets in a new multi-dimensional classification space. Iteration of these steps enables embodiments (method and system) to progressively refine the evaluative assessment through progressive comparisons. Each prior comparison enables the application (method/system) to discard unlikely classifications, and confirm or further explore more likely classifications. Therefore, through the step of refining, the multi-dimensional classification space progresses into another classification space, and at any given assessment junction, represents interim evaluative hypotheses that are devised and evaluated en route to the selection of a final diagnosis. An "evaluative hypothesis" as used herein, means a prediction of a final evaluative assessment. For example, an evaluative hypothesis can be a predicted disease state. Comparison of the individual's progressive processed data with the stored data in the classification space enables a system of the present invention to refine an evaluative assessment. In an example embodiment, a system can analyze an individual's processed data and note a particular trait or phenomenon in the medical imagery. By comparing the individual's current image data to pathologic imagery in a stored data set, wherein the trait or phenomenon is also noted in the pathologic imagery, a system of the present invention may refine an evaluative assessment or a diagnosis for an individual. Generally speaking, comparing the assessment data set to stored data enables an embodiment (system and method) to sort an individual's imagery data into pathological or physiological classifications.

In certain embodiments, the refining step further comprises optimizing a captured imagery, recording a captured imagery, or a combination thereof. After it is prepared, the imaging data is fit into one or more multi-dimensional classification spaces. This enables a user to track the progressive refining of the evaluative assessment through a progression of imagery.

Any pathophysiology, if present, is noted, as is any imagery indicating gradations of a healthy organ system. The imagery is used to automatically select one or more other image modes, progressively evaluating such content against current decision juncture. The application (system/method of the present invention) points out the way by visually showcasing image regions pertinent to the evaluative assessment.

Further, an optional log and/or window displays an evaluation space unfolding from current to next evaluative boundary "landscape". Such space may encompass thousands or more successive multi-dimensional refinements, a visual bi- or multi-partite tree structure could iterate from one relevant decision boundary landscape to the next. Overlapping or separated bounds may occur, depending upon medical diagnostic space. As some boundary decision tests may yield medically sporadic results, specific of such evaluation boundaries may be pointed out or able to be rerun upon command. To indicate assessment risk in distinguishing more or less populated delineations of such medical diagnostic space, where there may be rare conditions or pathology, color schemes or dot-density or other visual or audio effects may be used.

A resulting comparison against stored data is automatically used to refine evaluative assessments. In certain embodiments, refining the evaluative assessments is concurrent with a further imaging study of the individual's organ system. These further imaging studies comprise acquiring imaging data through fine-tuning angles, varying image modes, and successive imaging views, for example a view of particular vasculature.

At the close of a patient study, evaluative hypotheses have been successively iterated such that prioritized evaluation results. That is, evaluative hypotheses that are determined to be false are discarded and other evaluative hypotheses have been confirmed by cross-assessment with known imagery or stored data.

Since current imagery is thus already optimized for any morphological, pathological, or physiological content, image production automation can effectively increase.

In example embodiments, the evaluative assessment is based on an echocardiographic assessment. In example embodiments, certain physical parameters of the heart are studied and compared over time or across patient populations. Such physical parameters include wall thickness, wall size, heart rate, cardiac output, stroke volume, ejection fraction, systolic or diastolic function, the diameter, dimensions, and geometry of the heart or the heart or its constituent chambers, valve function, and chamber volume.

Any technician or user can use application captured imagery as is for production, or possibly further optimize or label the imagery prior to production with regard to each view. Imagery is recorded, or alternately an embodiment sends (i.e., electronically communicates or otherwise transmits) image data to one or more configured email addresses, a Cloud computing device, a repository, a server, or other internet address and the like via a secure public network connection.

The present invention also relates to a computer system to aid in the medical imaging of an individual. The computer system includes a recognition module configured to recognize the organ system to be studied, an assessment module configured to determine morphology and physiology of recognized organ system or anatomic structure, an evaluation module configured to identify abnormalities or pathologies, if present, in the morphology and physiology of said anatomic structure, a showcase module configured to visually emphasize, abstract, focus and/or animate an image region pertinent to evaluative assessment, an optimization module configured to post-process images, a transmission module configured to send images and information to target addresses, and a recommendation module configured to recommend to a user a modification of views, angles, image modes or combinations thereof.

In certain embodiments, the evaluation module identifies any abnormalities or pathologies in the morphology and physiology of the health gradations of an anatomic structure, or any abnormalities in the health metrics of the individual.

In certain embodiments, the showcase module applies textures to the imagery for user visibility purposes. In an example embodiment, textures allow a user to distinguish different functionalities, such as, stenotic tissue from healthy tissue. In alternate embodiments, the showcase module utilizes color to distinguish between structures or components of the organ system that exhibit different functionalities. In certain embodiments, the application animates the motion of the organ system, creates one or more freeze-frames of the organ system, abstracts the shape, boundaries, colors or textures of the organ system, or a combination thereof In an example embodiment, the abstracted shape of the organ system, or of a portion of the organ system indicates the effective power of pulse force against resistance. In another example embodiment, color is utilized in an organ system abstraction to demonstrate the extent of oxygenation of hemoglobin delivered by an artery.

In certain embodiments, images can be tuned by the recommendation module by, for example, fine angle modification, switching between sensors and camera view, moving to a new portion of the organ system for further assessment, enlarging a view, or adjusting image output, for example through increasing or decreasing gain, brightness, contrast or noise.

Another embodiment of the present invention comprises an imagery selection module configured to choose images as surrounding the showcased region, additionally any such evaluation-relevant images of various image modalities.

In certain embodiments, the transmission module sends (i.e., electronically communicates or otherwise transmits) an assessment to target addressees, receives confirmation, and logs data.

In certain embodiments, the optimization module post-processes images and prioritizes evaluative content in showcase regions.

In another embodiment of the invention, the computer system triggers an alert based on an evaluative assessment, evaluative hypothesis, or diagnostic hypothesis. A refined evaluative assessment, or a diagnostic hypothesis which has been decided with confidence, can trigger an alert if such a evaluative assessment or diagnostic hypothesis is designated to be of important or urgent status. The classification can be designated as important or urgent by the computer application, by the individual, by the user, by a health care professional and the like. The alert is sent to the individual, a member of the individual's family, an individual's health proxy, a healthcare provider, one or more persons designated by the individual, or a combination thereof. In certain embodiments, the application automatically triggers an alert, for example as an email, to be sent to the designated recipient. Example embodiments of evaluative assessments or diagnostic hypotheses that can be designated as carrying important or urgent status include (a) if the vasculature is found to be too dense in a particular region (possibly indicating an undiscovered tumor) or (b) if there is less fluidic supply on one side of the face relative to the other (one predictor of a future stroke). In alternate embodiments, a evaluative assessment or diagnostic hypothesis can be designated as having an important or urgent status based upon a user's or individual's desire, rather than medical need. For example, if an individual wishes to increase cardiac output by 1%, a trigger can be set up to provide an alert when the goal is reached. In certain embodiments of the invention, the computer-based method of imaging an organ system further comprises triggering an alert as described above, wherein the alert is generated based on an evaluative assessment.

The application design framework of the computer system and methods described herein promotes medical progress in the detection and/or diagnosis of many diseases. Production imagery can also be forwarded to a public or private network repository for anonymous analysis. A growing source of medical imagery with open, limited, or restricted access could enable medical, research and training experts to improve the progress and characterization of many diseases.

The application assists a user, technician, sonographer, or physician in operating a workstation's transducer probe on a patient or individual and simultaneously in managing production of health images. In an example embodiment, the user can manage imagery production and control other aspects of image capture through a head and/or face based user interface, wherein the head and/or face based user interface utilizes eye gaze, facial gestures, and/or head gestures for hands free operation of an imaging device. In another embodiment, rather than having to simultaneously manipulate an echocardiography machine's keyboard, the user could rely on the application's ability to recognize and identify the individual's organ structures and organ function, for example in the examination of cardiac structure and function. Thus, pertinent morphology, physiology, or pathology could be showcased, by coming into viewing "focus" automatically.

In an example embodiment, a showcase region displays while viewing a parasternal long view on a computer screen, akin to what a point-and-shoot camera does with facial recognition software. Thus, the ability for this type of recognition to occur could decrease the number of misdiagnoses from echocardiograms and improve the rate of capturing of more useful imagery content for diagnostic and prognostic purposes. Also, image tradeoffs of frame rate, noise, gain, brightness and other typical adjustment parameters could be consistently optimized for the content within a focus region rather than in areas of imagery less pertinent to diagnosis or critical evaluation.

In another example, planar views in an echocardiogram typically need to be recognized visually by the user, technician or physician performing the cardiac echo. In order to recognize such a view, similar to a sonographer mentally processing and determining what is viewed on a computer screen, any imagery in this view is compared to known heart views and then identified based on those views.

In further embodiments of the invention, the computer system further comprises an application setup module configured to enable target email addresses to be set, edited, deleted, and/or added. For an individual or patient, identifying data records can be entered, logged and/or edited. Such data records include, for example, name, visit number, photos, target medical facility, patient ID, insurance data, patient type (for example, whether the patient is a cardiac patient or a pulmonary patient), group (for example a user-defined parameter, or alternately an insurance group type), previous evaluation results, past medical history, past surgical history, and/or other conditions. Target email addresses could vary, for example, by patient type, group, insurance, and medical facility. The setup module can also start a new individual evaluation, and can configure application options.

Log files can securely vary by patient type, group, diagnostic evaluations, and network location. Internal databases format facilitates any custom reports in general.

In certain embodiments, the computer system further comprises a module configured to upload imagery, information and identifying data to the Cloud or a Cloud computing device. In particular embodiments, this uploading action occurs with a timestamp. In certain embodiments, uploading information further comprises adjusting data records or fields in order to comply with healthcare regulations, for example HIPAA regulations.

In certain embodiments, the application requires a user ID and password to invoke, since the application can be run anywhere and involves confidential patient data.

In another embodiment, the computer system auto-assesses an individual's studied organ system.

An image mode should be assessed visually. Assessing occurs via comparing against known cardiac imagery in this image mode or available other. Such a comparison is made by adjusting imagery then balancing out across a developed range of diverse look-alikes, then identifying the closest similarity.

Further assessment can be made by invoking another image mode or other available image mode for further assessment. In some embodiments, a user adjusts any imaging parameters and controls, such as frame rate, to better evaluate. Image modes automatically cycle, based upon context.

Throughout the health imaging study of the individual, evaluation of the organ system, for example the heart or brain, occurs. In an example embodiment, the application compares an individual's heart to records of data of previously recorded hearts, for example, healthy hearts and/or pathologic hearts, and the associated pathophysiology, morphology and functioning thereof. Perceived health levels, conditions and pathology of the individual's heart are recognized, and then utilized to predict evaluative hypotheses, which are identified relative to known cardiac diagnoses and healthiness aspects in prior patients.

Advantages of the present invention can include discovering less-than-optimal supply of blood to brain in evaluating vascular functioning in the head and neck. Thus, the present invention has an application in forecasting potential stroke or trans-ischemic attack. Other advantages can include discovering potential tumor sites by evaluating body vasculature, or assessing tumor growth or shrinkage that has occurred since a prior evaluation. Such an evaluation can also appraise vascular muscle fitness.

In certain embodiments of the invention, an individual is ranked on a spectrum based on one or more metrics, one or more diagnoses, or a combination thereof. The spectrum is an ordered group of other individuals. The spectrum of individuals can comprise like individuals, the general population, a set of individuals grouped by location, occupation, sedentary level, age, gender, exercise habits, diet, family ties, origins within a particular gene pool, or alternately a population group identified by the individual or the user. Examples of the order in which the spectrum is organized include severity of disease state. Alternately, a grouping of people may be ranked across multiple spectra, for example, spectra including morbidity, comorbidity, metastasis, cancer recurrence, age, gender, probability for healing, expected time for healing, mortality, and any other aspect of the possible spectra of individuals identified above. Examples of metrics that can be used in ranking individuals along a spectrum include, but are not limited to, cardiac morphology, physiology, and pathophysiology, levels of nutrient delivery. Cross-assessment of the individual on the spectrum enables updating and/or refining the evaluative assessment. For example, a pacemaker is not in itself an issue, but should be noted (along with any surrounding trauma). Other modalities such as EKG input feed or bubble study may be cross/assessed as well.

An example embodiment of the present invention 100 is shown in FIG. 1. At the start for a new individual 101, the evaluation assessment is null. The application (system/method 100) refines evaluative assessment throughout the study. The application automates identification and recognition 105 of an organ system. The application then assesses 109 an organ system in terms of its structures or functionality and generates an assessment data set. In certain embodiments, the organ system characteristics 113 are noted. In step 117, the assessment data set is compared to data in a multi-dimensional classification space. In certain embodiments, the comparison results in an evaluative assessment 121 which is showcased by step 125.

The evaluative assessment can identify one or more locales of any perceived issues. The locale can in certain embodiments be a whole organ or alternately any portion thereof, or can be a cross-assessment of two different organ systems, for example cerebral spinal fluid to blood cycling. As study continues, further angles or views with ensuing mode imagery are uncovered and thus potential evaluative hypotheses are progressively changed, re-weighted or pruned towards final assessment outcome.

As the application or system 100 derives the evaluative assessment, image subregions corresponding to its pertinent identification may be emphasized in the display, for example via highlighting. For example, if evaluative assessment weighs towards mitral regurgitation, in 2-D and color Doppler modes the showcase region can bound the mitral valve and any relevant portions of left atrium. Alternately, arrows or another mechanism to emphasize the subregion are displayed.

In order to indicate progression from hypothesis to a final assessment made with confidence, showcase bounds evolve into displaying focus bounds. In an example embodiment in which both dilated cardiomyopathy and ventricular hypertrophy are early working hypotheses, showcase bounds can display in alternative color, or alternately in dashed or blurred curves, and the evaluative assessment is refined by step 129. Upon yielding a confident assessment of dilated cardiomyopathy, region bounds can then display as solid, or alternately heavier weighted lined, to indicate progress of a devising an assessment. In certain embodiments, once a final assessment is devised, imagery optimization and recording 133 occurs in preparation for production capture. As one or more focus regions are prioritized, image post-processing automatically invokes for this capture batch. Such batch can also include various select views, angles, and image modalities pertinent for this diagnostic assessment.

In certain embodiments, the Applicants' method 100 also comprises making recommendations 137 to the individual based on imagery analysis.

In certain embodiments, this capture batch uploads to a pre-determined target address in a report 141. In embodiments requiring urgent handling of incoming imaging data, the data can be sent via email or other electronic communication, and identified by a header. The body of the email can be defined by any individual with identifying information previously specified via Setup or by a pre-set fielded template.

A corresponding log entry is created for operational/security/recovery purposes. When successfully delivered to/received by email addressee, a return confirmation is logged by the application and accessible onscreen to user if application option pre-set.

In certain embodiments, when the medical imaging study is finished, a completion email is sent. In certain embodiments, the email contains summary test results for the individual, a reference to all such previously-sent imagery, and/or all capture batches. In embodiments where an application option were pre-set to "do not send until complete" for this individual or patient type, all capture imagery is sent via this completion email instead.

In embodiments of the invention, the application described herein factors or tracks visual properties of each echo machine type, so to evaluate the individual with accuracy.

The present invention allows multiple views, angles, image modes, or combinations thereof to be shown in a gallery format, for example by showing tiles.

In certain embodiments, the application indicates to user how to move the probe or imaging device. For example, within a view such as frontal forehead or Apical 4-chamber, the application can visually suggest fine physical angular adjustments of probe.

To move to the next view or return to the previous view, application indicates which view and how to achieve it.

As some image modes require sampling boxes to be applied, the application automatically does so when needing assessment or (re)bounding showcase/focus region.

In certain embodiments, an application switch can track an experienced user versus less experienced users. The application can therefore show comparative imagery and/or evaluative hypotheses (leading to evaluative diagnosis) to sets of users. For some sets of experienced users, more autonomy and informational display may be enabled. In some embodiments, each user's evaluative assessment and captured imagery is stored and retrievable for multi-user operation.

Figure 2:
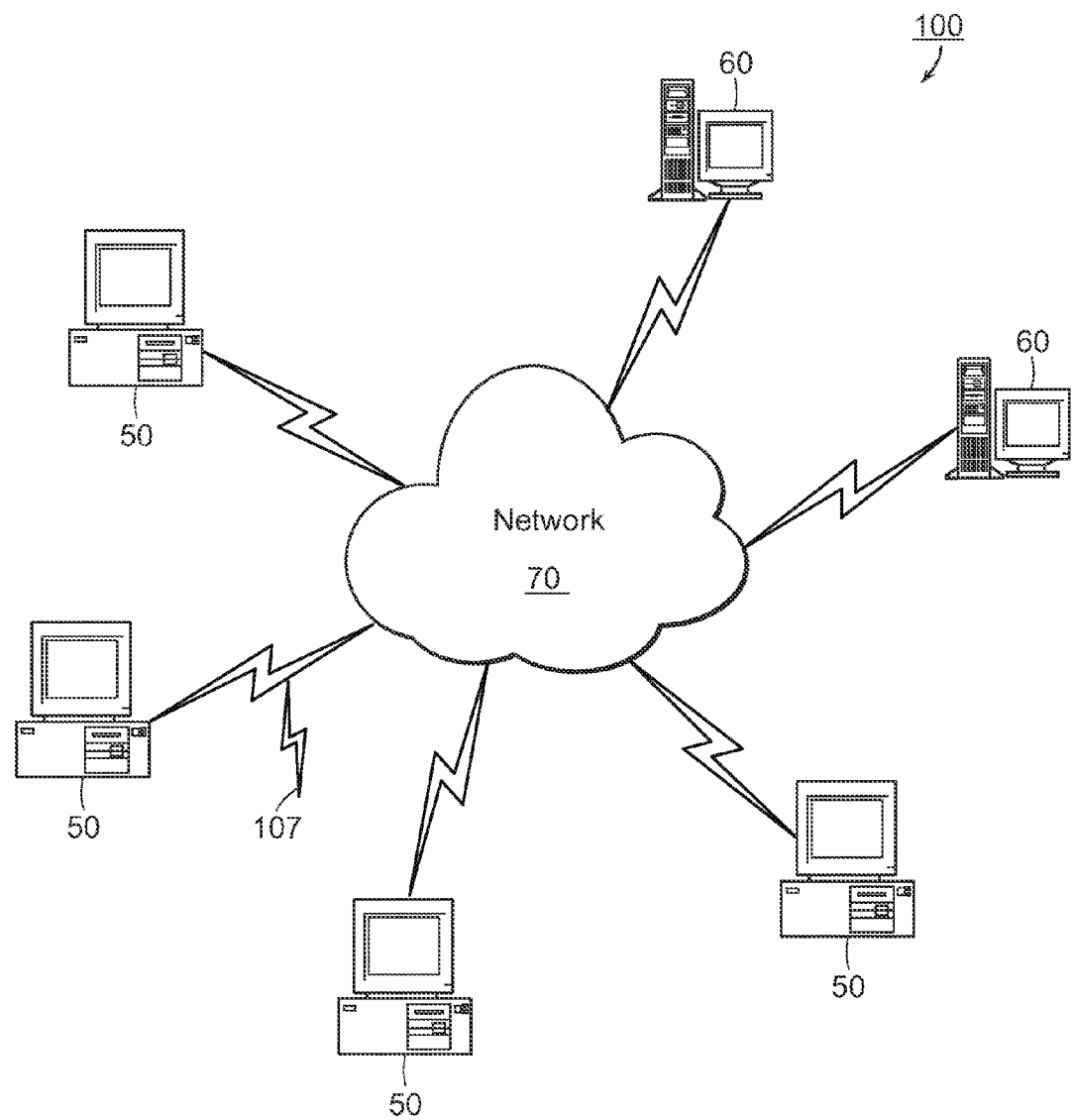
FIG. 2 is a schematic view of a computer network environment in which embodiments of the present invention may be deployed.

FIG. 2 illustrates a computer network or similar digital processing environment of applicants invention 100 in which the present invention may be implemented.

Client electronic devices 50 and server computers 60 provide processing, storage, and input/output devices executing application programs and the like. Client electronic devices 50 can also be linked through communications network 70 to other computing devices, including other client electronic devices/processes 50 and server computers 60. Electronic device 50 is any device including a processor, and can include a server, a computer, a laptop, a tablet, a smart phone, a cell phone and the like. In certain embodiments, electronic device 50 further includes one or more sensors, cameras, transducers or probes. In certain embodiments, electronic device 50 connects to the Internet in order to upload data, an evaluative assessment, or the like to a health care provider, or alternately sends such information via email. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 3:
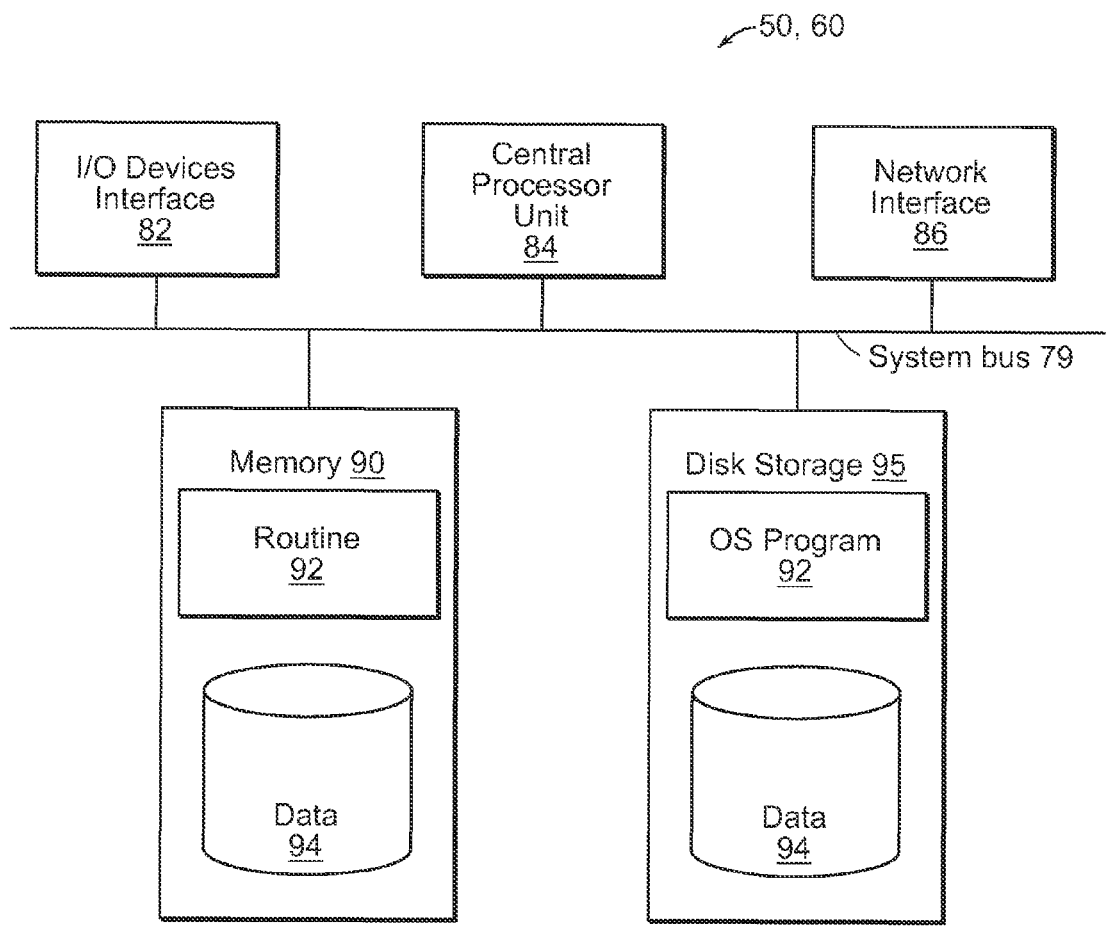
FIG. 3 is a block diagram of computer nodes or electronic devices in the computer network of FIG. 2 embodying the present invention.
Figure 4:
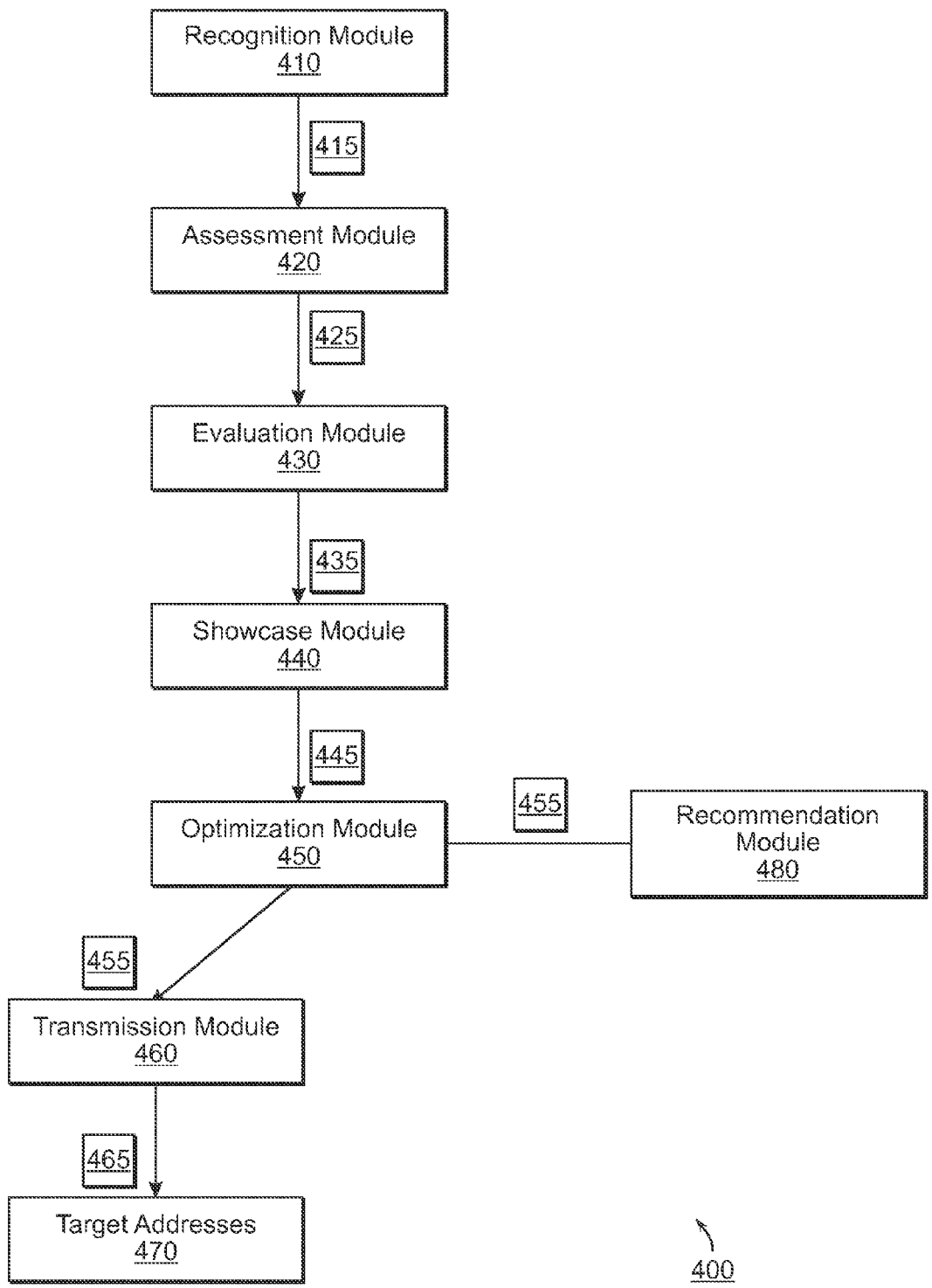
FIG. 4 is a diagram of one embodiment of a computer system that can be used in a electromagnetic imaging study of an individual.

FIG. 3 is a diagram of the internal structure of a computer (e.g., client electronic device 50 or server computers 60) in the computer system of FIG. 4. Each electronic device 50, or server computer 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the electronic device 50, server computer 60. Network interface 86 allows the computer to connect to various other devices attached to a network (e.g., network 70 of FIG. 2). Memory 90 provides volatile storage for computer software instructions 92 and data 94 used to implement an embodiment of the present invention (e.g., the computer health imaging code 100, 400 detailed above and below in FIGS. 1 and 4). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more USB, DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

FIG. 4 is an embodiment of a computer system 400. The computer system comprises a recognition module 410, which sends anatomic structure 415 to an assessment module 420. Assessment module 420 determines morphology and physiology 425 of the anatomic structure, then sends morphology and physiology 425 to evaluation module 430. The evaluation module 430 identifies the abnormalities or pathologies 435 present in the anatomic structure then sends abnormalities or pathologies 435 to showcase module 440. The showcase module enhances the images 445 in a manner defined in Setup, then sends images 445 to an optimization module 450. The optimization module can then send post-processed images 455 to a recommendation module 480 for imaging modification, or alternately to a transmission module 460. Recommendation module 480 results in modification of images to send back to the optimization module. Transition module 460 sends images, information, or individual data 465 to one or more target addresses 470.

Figure 5:
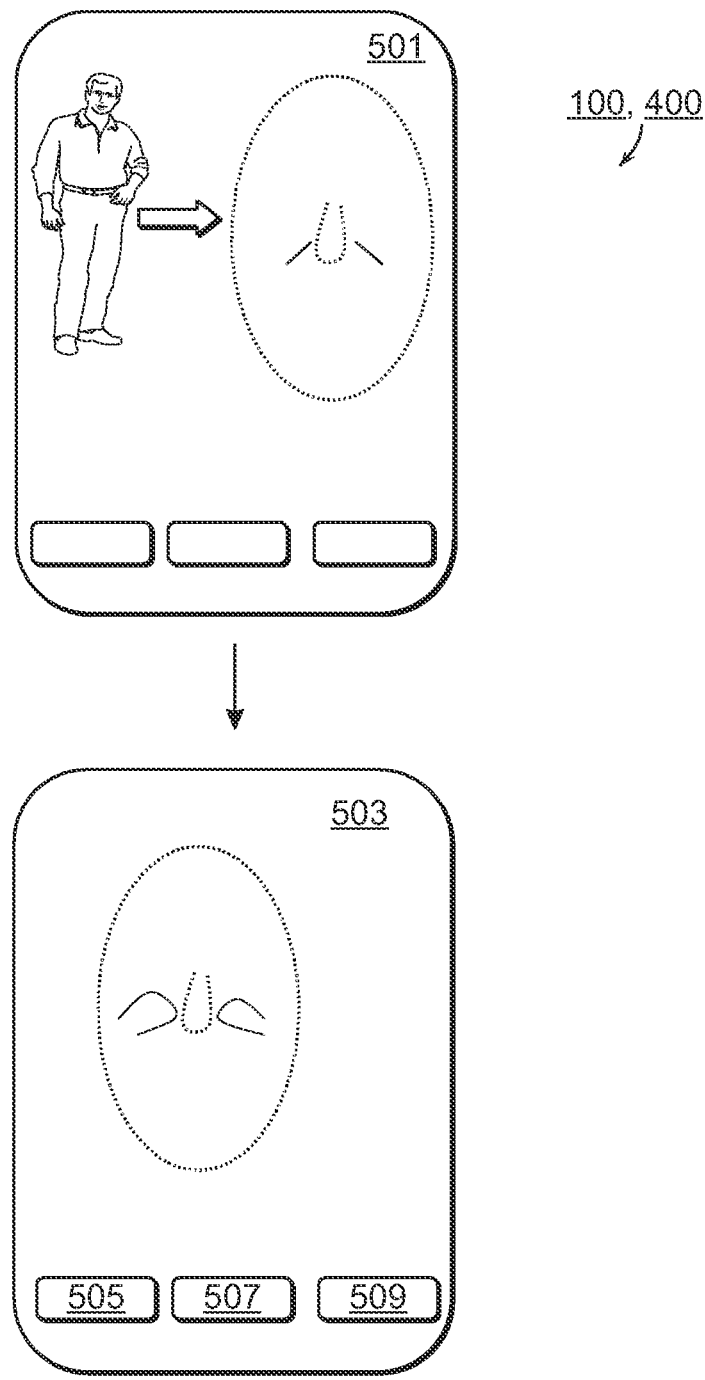
FIG. 5 is a schematic view of a display and user interface of the computer system in one embodiment of the present invention.

FIG. 5 shows an embodiment of a display of the computer system of the present invention 100, 400. In this example embodiment, the display is shown on a smart phone or tablet screen. An initial display 501 is rendered upon opening the application (system/method 100). From the initial display 501, the view quickly zooms in on camera-viewed region. The display highlights via outline or shadow the sample artery highlighted in cycle (t). Automated zoom paves the way for later suggested user camera navigation. Zoom can occur, in example embodiments via a double tap or pinch. In an example embodiment, the electronic device generates an audio sound wherein the heart pulse is approximated and played. As an example, view 503 shows a wavefront pulse shape, for example, in facial vasculature. Cycle(t) wave fronts are displayed via animated pulse/contract cycles, for example pulse dribbling. At stage 503, the electronic device plays an audio sound of a finer approximation of the heart pulse. In alternate embodiments, the heart pulse is displayed via visual waveforms.

Tabs or buttons 505, 507, and 509 are selectable touch controls. In an example embodiment, tab 505 provides or otherwise operates a fitness assessment, tab 507 provides a comparison against a data set, and tab 509 operates to provide the user with more information or more options. Table 1 shows example embodiments of visual displays of the invention.

TABLE 1

Application Displays

| Version | Fitness 505 | Compare Against 507 | More 509 |
|---|---|---|---|
| V1 | Increase energy by increasing heart rate. Display squared implication with respect to beat frequency) | Ideal average across population | Show baseline energy/cycle. User option: consent to forward data to repository? |
|  | Increase 1% | Past self-history. Display most recent assessment and date. | Show efficiency metrics (e.g. variance, slope powering up/down) Alert if correlation with pathology |
| V2 | Link activates upon energy improvement. | Designated buddy | quad muscle fitness |
|  | Sample energy accomplishment w/such "improvement", e.g. road race time. | Assess "wellness engine" age. | Comparison of earlier assessment to current view |
|  | Assess fitness of particular organ system | Assess pressure compared to celebrity or individual type | Assess EKG equivalent |
| V3 | Assess hard-to-see body parts (i.e. deltoids) via mirror, evaluation bounced rays, or via 2 devices with ray transmittal. | Multiple buddies or fitness partners | Show "current(t) -> energy" implications: axial vs rotational Audio output: music synchronized to personal cycle |

While this invention has been particularly shown and described with references to example embodiments thereof, it will be understood by those skilled in the art that various changes in form and details may be made therein without departing from the scope of the invention encompassed by the appended claims.

What is claimed is:

1. A computer-based method of imaging an organ system or an anatomic structure in an individual, the method comprising the steps of:
    while an imaging device is being used on an individual:
    a) in a recognition module, executable by a processor, automating identification of and recognizing an organ system or an anatomic structure from imaging data acquired through the imaging device;
    b) in an assessment module, executable by the processor, assessing the identified and recognized organ system or anatomic structure of the individual to produce an assessment data set;
    c) in an evaluation module, executable by the processor, comparing the assessment data set of step b) to one or more comparison data sets in a multi-dimensional classification space to generate an evaluative assessment of the organ system or anatomic structure, wherein the evaluative assessment comprises a classification of the imaging data;
    d) in a recommendation module, executable by the processor, recommending to a user a modification of a view, an angle, an image mode or a combination thereof; and
    e) refining the evaluative assessment of step c) by repeating steps b), c), and d).

2. The method of claim 1, wherein step e) further comprises optimizing a captured imagery, recording a captured imagery, or a combination thereof, wherein the imaging data is fit into one or more multi-dimensional health classification spaces.

3. The method of claim 1, wherein the organ system is the individual's cardiovascular system, brain, or a combination thereof.

4. The method of claim 1, wherein the method further comprises animating the motion of the organ system or anatomic structure, creating one or more freeze-frames of the organ system or anatomic structure, abstracting the shape, boundaries, color, textures, or a combination thereof of the organ system or anatomic structure.

5. The method of claim 1, wherein the imaging device comprises one or more sensors.

6. The method of claim 5, wherein the one or more sensors is a magnetic sensor, gyroscope, accelerometer, electrocardiography sensor, electromyography sensor, camera, RGB sensor, green light sensor, red light sensor, blue light sensor, motion sensor, near infrared camera, infrared camera, thermal camera, GPS or WiFi.

7. The method of claim 1, further comprising ranking the individual on a spectrum based on one or more metrics, one or more diagnoses, or a combination thereof, wherein the spectrum is an ordered group of other individuals.

8. The method of claim 1, further comprising identifying metrics of the individual based upon the evaluative assessment, wherein the metrics are saved and tracked over a period of time.

9. The method of claim 1, further comprising triggering an alert, wherein the alert is generated based on the evaluative assessment.

10. The method of claim 9, wherein the alert is sent to the individual, a member of the individual's family, an individual's health proxy, a healthcare provider, one or more persons designated by the individual, or a combination thereof.

11. A computer system to aid in a medical imaging study of an individual, the computer system comprising:
    while an imaging device is being used on an individual:
        a recognition module configured to recognize the individual's organ system or anatomic structure to be studied from imaging data acquired through the imaging device;
        an assessment module coupled to the recognition module and configured to determine morphology and physiology of the recognized organ system or anatomic structure;
        an evaluation module configured to identify abnormalities or pathologies in the determined morphology and physiology of said organ system or anatomic structure, if present;
        a showcase module configured to visually emphasize, abstract, focus, animate, or a combination thereof an image region pertinent to evaluative assessment;
        an optimization module configured to post-process images;
        a transmission module configured to send the post-processed images and information to target addresses; and
        a recommendation module configured to recommend to a user a modification of a view, an angle, an image mode or a combination thereof.

12. The computer system of claim 11, wherein the organ system is a cardiovascular system, brain, or a combination thereof.

13. The computer system of claim 11, further comprising a sensor module configured to connect one or more sensors.

14. The computer system of claim 13, wherein the one or more sensors is a magnetic sensor, gyroscope, accelerometer, electrocardiography sensor, electromyography sensor, camera, RGB sensor, green light sensor, red light sensor, blue light sensor, motion sensor, near infrared camera, infrared camera, thermal camera, GPS or WiFi.

15. The computer system of claim 11, further comprising a ranking module configured to rank the individual based one or more metrics or one or more diagnostic classifications.

16. The computer system of claim 11, further comprising a tracking module configured to track metrics of the individual over a period of time, predict a next series of metrics, or a combination thereof.

17. The computer system of claim 11, further comprising a trigger module configured to trigger an alert based on an evaluative assessment.

18. The computer system of claim 17, wherein the alert is sent to the individual, a member of the individual's family, an individual's health proxy, a healthcare provider, one or more persons designated by the individual, or a combination thereof.

19. The computer system of claim 17, wherein the alert is sent to the individual, a member of the individual's family, an individual's health proxy, a healthcare provider, one or more persons designated by the individual, or a combination thereof.

* * * * *